(12) United States Patent
Huff (10) Patent No.: US 8,936,649 B2
(45) Date of Patent: Jan. 20, 2015

(54) ORTHOPAEDIC HIP PROSTHESIS HAVING FEMORAL STEM COMPONENTS WITH VARYING A/P TAPER ANGLES

(71) Applicant: DePuy Synthes Products, LLC, Raynham, MA (US)

(72) Inventor: Daniel N. Huff, Warsaw, IN (US)

(73) Assignee: DePuy Synthes Products, LLC, Raynham, MA (US)

( * ) Notice: Subject to any disclaimer, the term of this patent is extended or adjusted under 35 U.S.C. 154(b) by 0 days.

(21) Appl. No.: 13/629,950

(22) Filed: Sep. 28, 2012

(65) Prior Publication Data

US 2014/0094926 A1    Apr. 3, 2014

(51) Int. Cl.
*A61F 2/32* (2006.01)

(52) U.S. Cl.
USPC ............ 623/23.41; 623/22.4; 623/22.42; 623/22.43; 623/22.44

(58) Field of Classification Search
USPC .............. 623/22.11–22.16, 22.4–23.46
See application file for complete search history.

(56) References Cited

U.S. PATENT DOCUMENTS 5,004,476 A * 4/1991 Cook .................... 623/23.3
2005/0055103 A1* 3/2005 Badatcheff et al. ...... 623/22.42

FOREIGN PATENT DOCUMENTS

| DE | 202007005537 U1 | 8/2007 |
| FR | 2636837 A1 | 3/1990 |
| FR | 2853524 A1 | 10/2004 |
| FR | 2889444 A1 | 2/2007 |

OTHER PUBLICATIONS

European Search Report, European Application No. 13186391.2-1654, Jan. 17, 2014, 6 pages.

* cited by examiner

*Primary Examiner* — Yashita Sharma
(74) *Attorney, Agent, or Firm* — Barnes & Thornburg LLP (57) ABSTRACT

A femoral prosthesis for use during performance of a hip replacement procedure includes a plurality of femoral stem components in a range of various sizes and a plurality of femoral head component in a range of various sizes. The anterior/posterior stem taper angle of the femoral stem component varies across its range of sizes.

13 Claims, 6 Drawing Sheets

ORTHOPAEDIC HIP PROSTHESIS HAVING FEMORAL STEM COMPONENTS WITH VARYING A/P TAPER ANGLES

TECHNICAL FIELD

The present disclosure relates generally to an orthopaedic hip prosthesis, and more particularly to orthopaedic hip prosthesis having femoral stem components with varying A/P taper angles.

BACKGROUND

During the lifetime of a patient, it may be necessary to perform a joint replacement procedure on the patient as a result of, for example, disease or trauma. The joint replacement procedure may involve the use of a prosthesis which is implanted into one of the patient's bones. In the case of a hip replacement procedure, a femoral prosthesis is implanted into the patient's femur. Such a femoral prosthesis typically includes a spherically-shaped head component which bears against the patient's natural or prosthetic acetabulum, along with an elongated intramedullary femoral stem component which is implanted in the patient's femur. To secure the femoral stem component to the patient's femur, the intramedullary canal of the patient's femur is first surgically prepared (e.g., broached) such that the femoral stem component may be subsequently implanted therein.

In some designs, the femoral stem component is implanted in the patient's femur by use of cementless fixation. One type of such a design is known as a 'fit and fill' stem component. The rationale of such a design is that contact between the stem and bone tissue of the patient is increased relative to other designs and, therefore, provides fixation stability and improved long-term bone remodeling of the patient's femur.

SUMMARY

According to one aspect, an implantable orthopaedic hip prosthesis assembly includes a femoral head component configured to articulate with a natural or prosthetic acetabulum of a patient. The femoral head component has a tapered bore formed therein. The hip prosthesis assembly also includes a plurality of femoral stem components having a tapered trunnion configured to be separately received into the tapered bore of the femoral head component. Each of the plurality of femoral stem components has a trunnion taper angle and diameter that is the same as each of the other of the plurality of femoral stem components. Each of the plurality of femoral stem components also has an anterior/posterior stem taper angle that is different from at least some of the other of the plurality of femoral stem components.

Each of the plurality of femoral stem components may also have a medial/lateral stem taper angle that is the same as each of the other of the plurality of femoral stem components.

Each of the plurality of femoral stem components may also have a medial/lateral cross sectional stem shape that is the same as each of the other of the plurality of femoral stem components.

In an embodiment, a first femoral stem component of the plurality of femoral stem components is longer than a second femoral stem component of the plurality of femoral stem components, and has a larger anterior/posterior stem taper angle than the second femoral stem component of the plurality of femoral stem components.

In such an embodiment, the first femoral stem component of the plurality of femoral stem components may have a medial/lateral stem taper angle that is the same as the second femoral stem component of the plurality of femoral stem components.

In another embodiment, a first femoral stem component of the plurality of femoral stem components is longer than a second femoral stem component and a third femoral stem component of the plurality of femoral stem components. The first femoral stem component may have a larger anterior/posterior stem taper angle than the second femoral stem component of the plurality of femoral stem components, while having an anterior/posterior stem taper angle that is the same as the third femoral stem component of the plurality of femoral stem components.

In such an embodiment, the first femoral stem component of the plurality of femoral stem components may have a medial/lateral stem taper angle that is the same as the second femoral stem component and the third femoral stem component of the plurality of femoral stem components.

According to another aspect, an implantable orthopaedic hip prosthesis assembly includes a first femoral stem component configured to be implanted into the intramedullary canal of a patient's femur. The first femoral stem component may include a first anterior/posterior stem taper angle and a tapered trunnion configured to be received into a tapered bore of a femoral head component. The tapered trunnion of the first femoral stem component has a first trunnion taper angle and a first trunnion diameter. The hip prosthesis assembly may also include a second femoral stem component configured to be implanted into the intramedullary canal of a patient's femur. The second femoral stem component may include a second anterior/posterior stem taper angle that is greater than the first anterior/posterior stem taper angle and a tapered trunnion configured to be received into a tapered bore of a femoral head component. The tapered trunnion of the second femoral stem component has a second trunnion taper angle that is the same as the first trunnion taper angle and a second trunnion diameter that is the same as the first trunnion diameter.

The first femoral stem component may include a first medial/lateral stem taper angle, and the second femoral stem component may include a second medial/lateral stem taper angle that is the same as the first medial/lateral stem taper angle.

The first femoral stem component may include a first medial/lateral cross sectional stem shape, and the second femoral stem component may include a second medial/lateral cross sectional stem shape that is the same as the first medial/lateral cross sectional stem shape.

In an embodiment, the second femoral stem component is longer than the first femoral stem component.

The first femoral stem component may further include a first medial/lateral stem taper angle, and the second femoral stem component may include a second medial/lateral stem taper angle that is the same as the first medial/lateral stem taper angle.

The hip prosthesis assembly may also include a third femoral stem component configured to be implanted into the intramedullary canal of a patient's femur. The third femoral stem component is longer than both the first and second femoral stem components. The third femoral stem component includes a third anterior/posterior stem taper angle that is greater than the first anterior/posterior stem taper angle and the same as the second anterior/posterior stem taper angle. The third femoral stem component also includes a tapered trunnion configured to be received into a tapered bore of a femoral head component, the tapered trunnion of the third femoral stem component having a third trunnion taper angle that is the same as the first and second trunnion taper angles and a third trunnion diameter that is the same as the first and second trunnion diameters.

In an embodiment, the third femoral stem component has a medial/lateral stem taper angle that is the same as the first and second medial/lateral stem taper angles.

According to yet another aspect, an implantable orthopaedic hip prosthesis assembly includes a femoral head component configured to articulate with a natural or prosthetic acetabulum of a patient. The femoral head component has a tapered bore formed therein. The hip prosthesis assembly also includes a plurality of femoral stem components having a tapered trunnion configured to be separately received into the tapered bore of the femoral head component. Each of the plurality of femoral stem components has a length that is different from at least some of the other plurality of femoral stem components. Each of the plurality of femoral stem components also has a trunnion taper angle and diameter that is the same as each of the other of the plurality of femoral stem components, an anterior/posterior stem taper angle that is different from at least some of the other of the plurality of femoral stem components, and a medial/lateral stem taper angle that is the same as each of the other of the plurality of femoral stem components.

Each of the plurality of femoral stem components may further have a medial/lateral cross sectional stem shape that is the same as each of the other of the plurality of femoral stem components.

In an embodiment, a first femoral stem component of the plurality of femoral stem components is longer than a second femoral stem component of the plurality of femoral stem components, and has a larger anterior/posterior stem taper angle than the second femoral stem component of the plurality of femoral stem components.

In another embodiment, a first femoral stem component of the plurality of femoral stem components is longer than a second femoral stem component and a third femoral stem component of the plurality of femoral stem components, has a larger anterior/posterior stem taper angle than the second femoral stem component of the plurality of femoral stem components, and has an anterior/posterior stem taper angle that is the same as the third femoral stem component of the plurality of femoral stem components.

BRIEF DESCRIPTION OF THE DRAWINGS

The detailed description particularly refers to the following figures, in which.

DETAILED DESCRIPTION OF THE DRAWINGS

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention.

Terms representing anatomical references, such as anterior, posterior, medial, lateral, superior, inferior, etcetera, may be used throughout this disclosure in reference to both the orthopaedic implants described herein and a patient's natural anatomy. Such terms have well-understood meanings in both the study of anatomy and the field of orthopaedics. Use of such anatomical reference terms in the specification and claims is intended to be consistent with their well-understood meanings unless noted otherwise.

Figure 1:
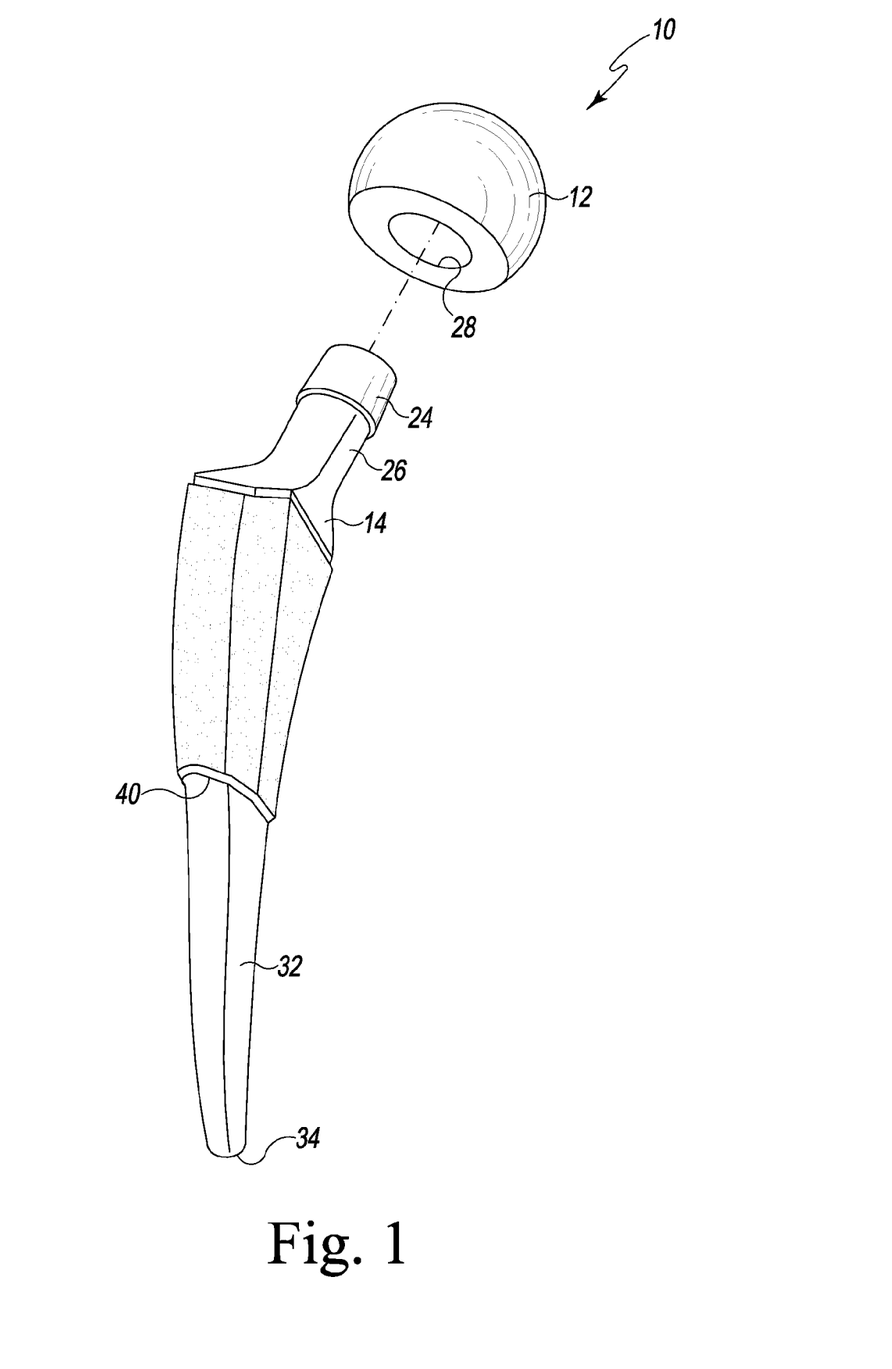
FIG. 1 is a perspective view of a femoral stem component and a head component of an orthopaedic hip prosthesis.
Figure 2:
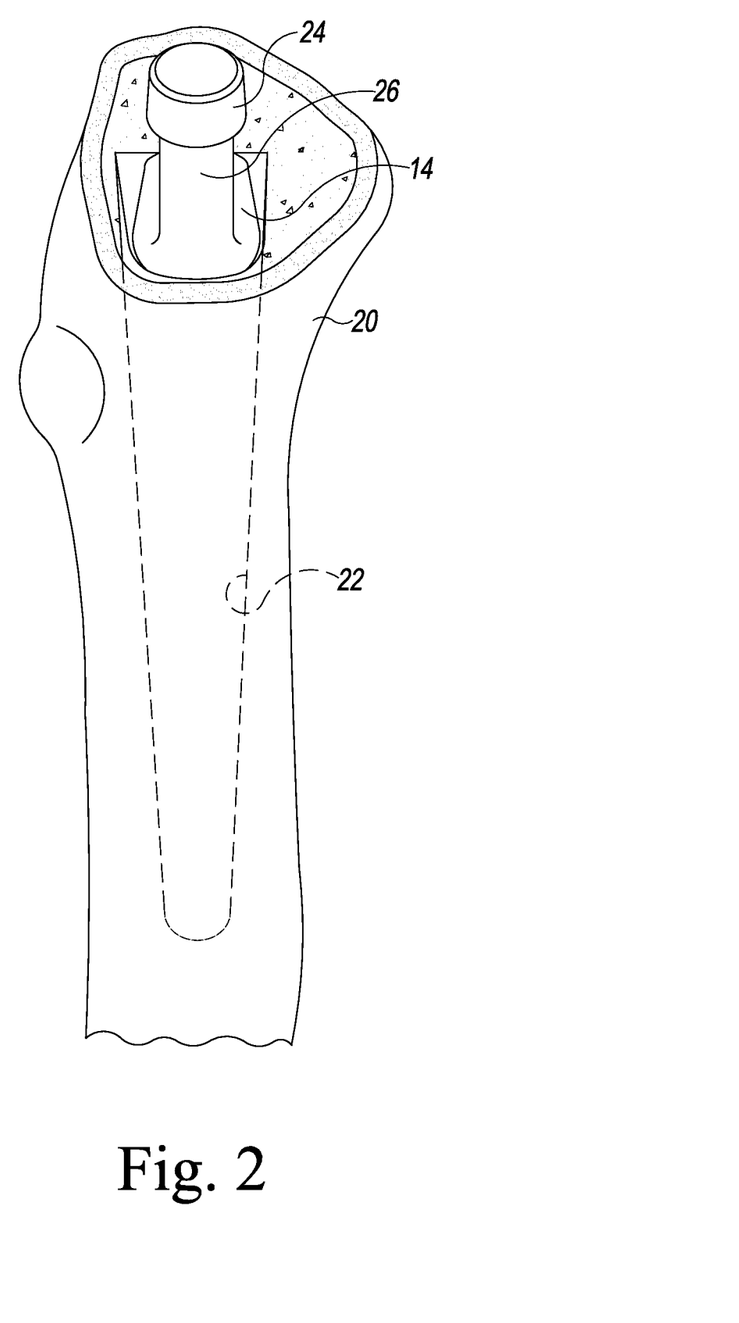
FIG. 2 is a perspective view showing the femoral stem component of FIG. 1 implanted into the femur of a patient.

Referring now to FIG. 1, there is shown an implantable orthopaedic hip prosthesis 10 for use during performance of a hip replacement procedure. The orthopaedic hip prosthesis 10 includes a femoral head component 12 and a femoral stem component 14. As shown in FIG. 2, the femoral stem component 14 is configured to be implanted into a femur 20 of a patient during a hip replacement procedure. In particular, the femoral stem component 14 is implanted into a surgically prepared (e.g., broached) intramedullary canal 22 of the patient's femur 20. The femoral head component 12 is secured to a trunnion 24 formed in the end of the elongated neck 26 of the femoral stem component 14. Specifically, as can be seen in FIG. 1, the femoral head component 12 has a tapered bore 28 formed therein into which the tapered trunnion 24 of the femoral stem component 14 may be advanced to taper lock the trunnion 24 (and hence the femoral stem component 14) and the femoral head component 12 to one another. When installed on the femoral stem component 14, the femoral head component 12 is positioned to bear on either the patient's natural acetabulum or a prosthetic socket which has been implanted into the patient's pelvis to replace his or her acetabulum. In such a manner, the orthopaedic hip prosthesis 10 and the natural or artificial acetabulum collectively function as a system which replaces the natural joint of the patient's hip.

In the illustrative embodiment described herein, the femoral stem component 14 is embodied as a 'fit and fill' type of femoral stem. As such, the femoral stem component 14 is embodied as a monolithic metal structure. The femoral stem component 14 may be constructed with an implant-grade biocompatible metal, although other materials may also be used. Examples of such metals include cobalt, including cobalt alloys such as a cobalt chrome alloy, titanium, including titanium alloys such as a Ti6Al4V alloy, and stainless steel. Such a metallic femoral stem component 14 may also be coated with a surface treatment, such as hydroxyapatite, to enhance biocompatibility. Moreover, the surfaces of the femoral stem component 14 that engage the natural bone, such as the outer surface of the proximal body 30, may be textured to facilitate securing the component to the bone. Such surfaces may also be porous coated to promote bone ingrowth for permanent fixation.

The proximal body 30 defines the midsection of the femoral stem component 14. As such, the elongated neck 26 extends superiorly and medially away from the proximal body 30, with the tapered trunnion 24 being formed in the superior/medial end of the neck 26—i.e., opposite the end that mates with the proximal body 30. A tapered stem 32 extends inferiorly away from the opposite end of the proximal body. The tapered stem 32 has a rounded distal end 34 that defines the inferior-most surface of the femoral stem component 14.

Figures 3, 4:
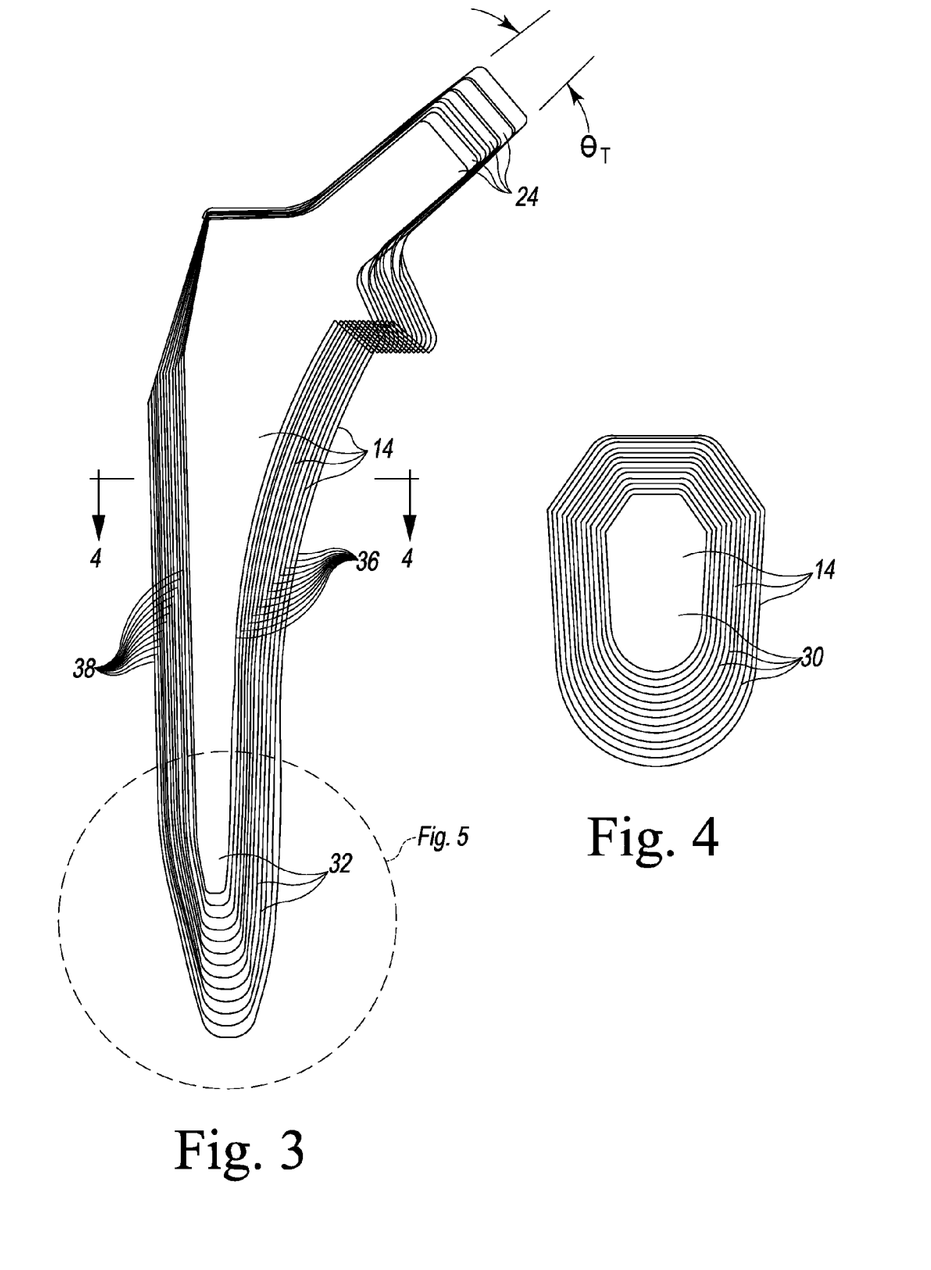
FIG. 3 is a diagrammatic medial/lateral view showing a number of femoral stem components with differing lengths superimposed upon one another.
FIG. 4 is a diagrammatic cross sectional view taken along line 4-4 of FIG. 3, as viewed in the direction of the arrows.

The femoral stem component 14 may be provided in a number of different configurations in order to fit the needs of a given patient's anatomy. In particular, the stem component 14 may be configured in various different lengths to conform to the patient's anatomy (e.g., a relatively long stem component 14 for use with a long femur 20, a relatively short stem for use with a short femur 20, etcetera). In one illustrative embodiment, the stem component 14 may be provided in thirteen different lengths (e.g., Sizes 0-12). As shown in FIG. 4, the size of the proximal body 30 likewise changes as a function of the size of the stem component 14. In particular, the size of the proximal body 30 increases as the size of the stem component 14 increases. However, as also shown in FIG. 4, the medial/lateral cross sectional shape of the stem's proximal body 30 remains the same throughout the range of sizes of the stem component 14. In other words, each of the differently sized stem components 14 has a common medial/lateral cross sectional shape, although the size (i.e., the area) of the cross sectional shape changes as a function of the stem length (i.e., longer stem components have a larger cross sectional size (but common shape) relative to smaller stem components).

Figure 6:
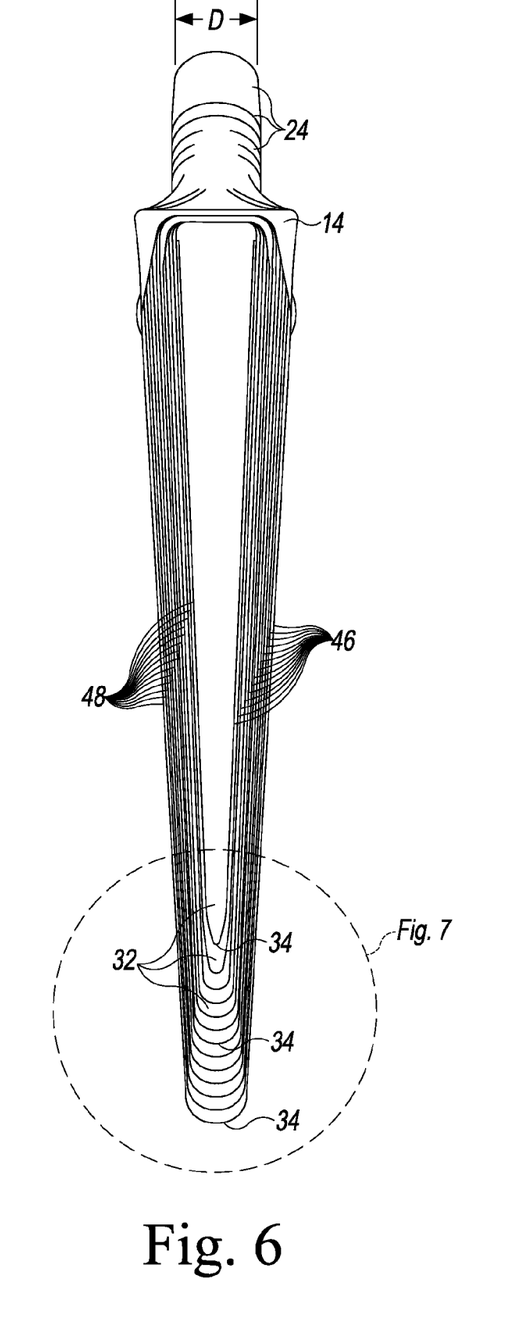
FIG. 6 is a view similar to FIG. 3, but taken from the anterior/posterior direction.

Like the femoral stem component 14, the head component 12 may be provided in varying diameters to fit the needs of a given patient's anatomy. Each of the differently-sized head components 12 is compatible with each of the differently-sized femoral stem components 14. In particular, as described above, the femoral head component 12 has a tapered bore 28 formed therein into which the tapered trunnion 24 of the femoral stem component 14 may be advanced to taper lock the trunnion 24 (and hence the femoral stem component 14) and the femoral head component 12 to one another. The geometry of the tapered bore 28 of each of the differently sized femoral head components 12 is identical. Specifically, each of the tapered bores 28 has taper angle and diameter that is the same as one another. Likewise, the geometry of the tapered trunnions 24 of each of the differently sized femoral stem components 14 is identical. In particular, as shown in FIG. 6, the trunnions 24 of each of the differently sized femoral stem components 14 has a diameter (D) that is the same as one another. As shown in FIG. 3, the taper angle (OT) of each stem component's trunnion 24 is the same across the range of sizes of the femoral stem components 14. Because the taper features of the head components 12 and stem components 14 are commonly sized across the range of component sizes, each of the differently-sized head components 12 is compatible with each of the differently-sized femoral stem components 14.

Figure 5:
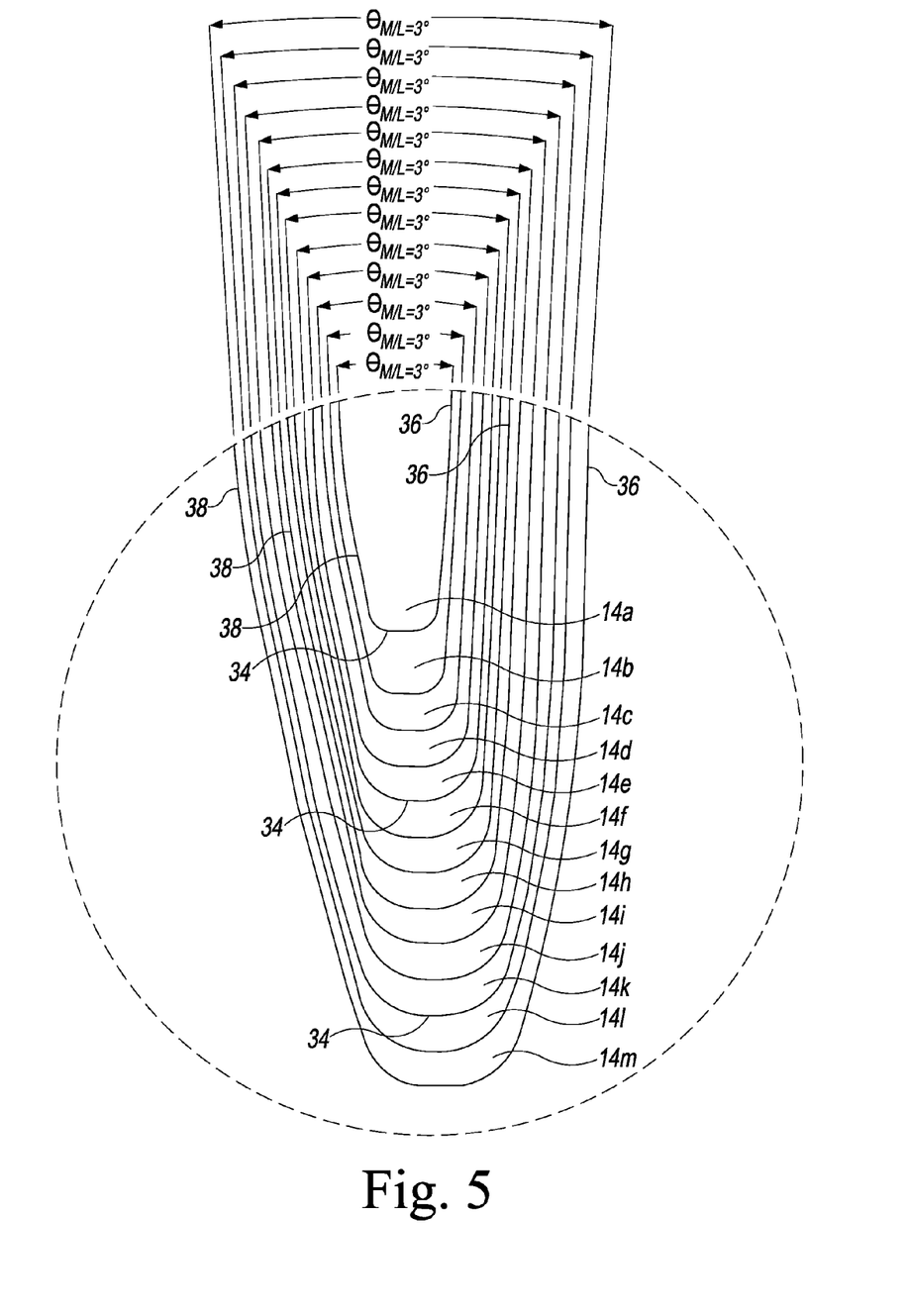
FIG. 5 is an enlarged diagrammatic medial/lateral view showing the distal ends of the femoral stem components in greater detail, with FIG. 4 being taken from FIG. 3 as indicated by the encircled area.

As shown in FIGS. 3 and 5, each of the differently-sized femoral stem components 14 has a common stem taper angle in the medial/lateral direction (i.e., a common medial/lateral stem taper angle). In particular, the femoral stem component's "medial/lateral stem taper angle" is defined herein as the magnitude of the angle formed by the medial edge 36 and the lateral edge 38 of the tapered stem 32. In other words, the femoral stem component's "medial/lateral stem taper angle" is the magnitude of the angle formed by the medial edge 36 and the lateral edge 38 of the portion of the femoral 14 stem component 14 extending between the inferior edge 40 of the proximal body 30 and the rounded distal end 34 that defines the inferior-most surface of the femoral stem component 14. As can be seen in FIG. 5, each of the differently-sized femoral stem components 14 has a common medial/lateral stem taper angle ($\theta_{M/L}$). In the exemplary embodiment described herein, each of the differently-sized femoral stem components 14 has a medial/lateral stem taper angle of 3° (i.e., $\theta_{M/L}$=3°).

Figure 7:
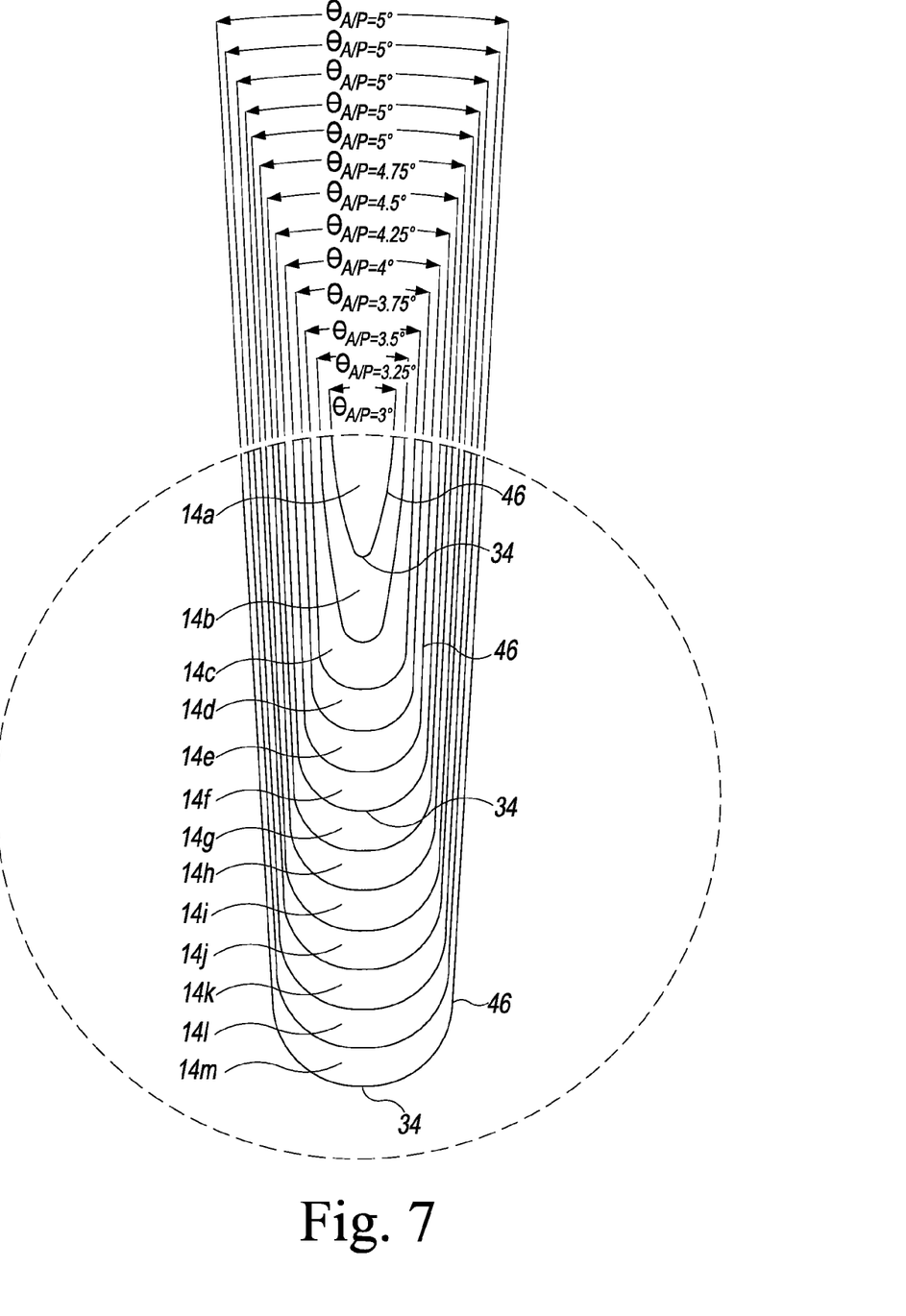
FIG. 7 is an enlarged diagrammatic anterior/posterior view showing the distal ends of the femoral stem components in greater detail, with FIG. 7 being taken from FIG. 6 as indicated by the encircled area.

In contrast, as shown in FIGS. 6 and 7, the stem taper angle in the anterior/posterior direction (i.e., the anterior/posterior stem taper angle) may vary across the range of differently-sized femoral stem components 14. In particular, the femoral stem component's "anterior/posterior stem taper angle" is defined herein as the magnitude of the angle formed by the anterior edge 46 and the posterior edge 48 of the tapered stem 32. In other words, the femoral stem component's "anterior/posterior stem taper angle" is the magnitude of the angle formed by the anterior edge 46 and the posterior edge 48 of the portion of the femoral 14 stem component 14 extending between the inferior edge 40 of the proximal body 30 and the rounded distal end 34 that defines the inferior-most surface of the femoral stem component 14. As can be seen in FIG. 6, each of the differently-sized femoral stem components 14 defines an anterior/posterior stem taper angle ($\theta_{A/P}$). The magnitude of the anterior/posterior stem taper angle ($\theta_{A/P}$) increases as the size of the femoral stem component 14 increases. That is, the magnitude of the anterior/posterior stem taper angle ($\theta_{A/P}$) of shorter femoral stem components 14 is smaller relative to the anterior/posterior stem taper angle ($\theta_{A/P}$) of the longer femoral stem components 14. Although, in the exemplary embodiment described herein, for certain larger sizes, the anterior/posterior stem taper angle ($\theta_{A/P}$) may remain the same.

For example, in the exemplary embodiment described herein, the smallest femoral stem component 14a (i.e., "Size 0") may have an anterior/posterior stem taper angle of 3° (i.e., $\theta_{A/P}$=3°). The next larger sized femoral stem component 14b (i.e., "Size 1") may have an anterior/posterior stem taper angle of 3.25° (i.e., $\theta_{A/P}$=3.25°), with the next larger size femoral stem component 14c (i.e., "Size 2") having an anterior/posterior stem taper angle of 3.50° (i.e., $\theta_{A/P}$=3.50°). Each progressively larger femoral stem component 14 (i.e., femoral stem components 14d, 14e, 14f, 14g, and 14h) may have an anterior/posterior stem taper angle ($\theta_{A/P}$) that is 0.25° larger than the previous size. As a result, the "Size 8" stem component (i.e., femoral stem component 14h) has an anterior/posterior stem taper angle of 4.75° (i.e., $\theta_{A/P}$=4.75°). In the exemplary embodiment described herein, each remaining femoral stem component 14 (i.e., femoral stem components 14i, 14j, 14k, 14l, and 14m) has a common anterior/posterior stem taper angle of 5° (i.e., $\theta_{A/P}$=5°).

As described above, the femoral stem component 14 has a constant medial/lateral stem taper angle of ($\theta_{M/L}$) across it range of sizes (e.g., $\theta_{M/L}$=3°), whereas its anterior/posterior stem taper angle ($\theta_{A/P}$) varies across its range of sizes (e.g., $\theta_{A/P}$ varies from 3°-5° across the component's range of sizes). As a result, desirable proximal fit of the femoral stem component 14 may be achieved while also ensuring the distal anterior/posterior thickness of the component doesn't inhibit the ability to implant the femoral stem component 14 into patient's having large canal flare index (i.e., type A). As such, the progressively changing anterior/posterior stem taper angle ($\theta_{A/P}$) of the differently-sized femoral stem components 14 allows for desirable proximal and distal fill. It also allows for femoral preparation with only a broach thereby reducing the complexity of the surgical process to implant the femoral stem component 14.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the apparatus, system, and method described herein. It will be noted that alternative embodiments of the apparatus, system, and method of the present disclosure may not include all of the features described yet still benefit from at least some of the advantages of such features. Those of ordinary skill in the art may readily devise their own implementations of the apparatus, system, and method that incorporate one or more of the features of the present invention and fall within the spirit and scope of the present disclosure.

The invention claimed is:

1. An implantable orthopaedic hip prosthesis assembly, comprising:
   a femoral head component configured to articulate with a natural or prosthetic acetabulum of a patient, the femoral head component having a tapered bore formed therein, and
   a plurality of femoral stem components having a tapered trunnion configured to be separately received into the tapered bore of the femoral head component, wherein each of the plurality of femoral stem components has (i) a trunnion taper angle and diameter that is the same as each of the other of the plurality of femoral stem components, and (ii) an anterior/posterior stem taper angle that is different from at least some of the other of the plurality of femoral stem components,
   wherein a first femoral stem component of the plurality of femoral stem components (i) is longer than a second femoral stem component and a third femoral stem component of the plurality of femoral stem components, (ii) has a larger anterior/posterior stem taper angle than the second femoral stem component of the plurality of femoral stem components, and (iii) has an anterior/posterior stem taper angle that is the same as the third femoral stem component of the plurality of femoral stem components.

2. The implantable orthopaedic hip prosthesis assembly of claim 1, wherein each of the plurality of femoral stem components further has a medial/lateral stem taper angle that is the same as each of the other of the plurality of femoral stem components.

3. The implantable orthopaedic hip prosthesis assembly of claim 1, wherein each of the plurality of femoral stem components further has a medial/lateral cross sectional stem shape that is the same as each of the other of the plurality of femoral stem components.

4. The implantable orthopaedic hip prosthesis assembly of claim 1, wherein the first femoral stem component of the plurality of femoral stem components has a medial/lateral stem taper angle that is the same as the second femoral stem component of the plurality of femoral stem components.

5. The implantable orthopaedic hip prosthesis assembly of claim 1, wherein the first femoral stem component of the plurality of femoral stem components has a medial/lateral stem taper angle that is the same as the second femoral stem component and the third femoral stem component of the plurality of femoral stem components.

6. An implantable orthopaedic hip prosthesis assembly, comprising:
   a first femoral stem component configured to be implanted into the intramedullary canal of a patient's femur, the first femoral stem component comprising (i) a first anterior/posterior stem taper angle, and (ii) a tapered trunnion configured to be received into a tapered bore of a femoral head component, the tapered trunnion of the first femoral stem component having a first trunnion taper angle and a first trunnion diameter,
   a second femoral stem component configured to be implanted into the intramedullary canal of a patient's femur, the second femoral stem component comprising (i) a second anterior/posterior stem taper angle that is greater than the first anterior/posterior stem taper angle, and (ii) a tapered trunnion configured to be received into a tapered bore of a femoral head component, the tapered trunnion of the second femoral stem component having a second trunnion taper angle that is the same as the first trunnion taper angle and a second trunnion diameter that is the same as the first trunnion diameter, and
   a third femoral stem component configured to be implanted into the intramedullary canal of a patient's femur, the third femoral stem component being longer than both the first and second femoral stem components and comprising (i) a third anterior/posterior stem taper angle that is greater than the first anterior/posterior stem taper angle and the same as the second anterior/posterior stem taper angle, and (ii) a tapered trunnion configured to be received into a tapered bore of a femoral head component, the tapered trunnion of the third femoral stem component having a third trunnion taper angle that is the same as the first and second trunnion taper angles and a third trunnion diameter that is the same as the first and second trunnion diameters.

7. The implantable orthopaedic hip prosthesis assembly of claim 6, wherein:
   the first femoral stem component further comprises a first medial/lateral stem taper angle, and
   the second femoral stem component further comprises a second medial/lateral stem taper angle that is the same as the first medial/lateral stem taper angle.

8. The implantable orthopaedic hip prosthesis assembly of claim 6, wherein:
   the first femoral stem component further comprises a first medial/lateral cross sectional stem shape, and
   the second femoral stem component further comprises a second medial/lateral cross sectional stem shape that is the same as the first medial/lateral cross sectional stem shape.

9. The implantable orthopaedic hip prosthesis assembly of claim 6, wherein the second femoral stem component is longer than the first femoral stem component.

10. The implantable orthopaedic hip prosthesis assembly of claim 9, wherein:
    the first femoral stem component further comprises a first medial/lateral stem taper angle, and
    the second femoral stem component further comprises a second medial/lateral stem taper angle that is the same as the first medial/lateral stem taper angle.

11. The implantable orthopaedic hip prosthesis assembly of claim 6, wherein the third femoral stem component has a medial/lateral stem taper angle that is the same as the first and second medial/lateral stem taper angles.

12. An implantable orthopaedic hip prosthesis assembly, comprising:
    a femoral head component configured to articulate with a natural or prosthetic acetabulum of a patient, the femoral head component having a tapered bore formed therein, and
    a plurality of femoral stem components having a tapered trunnion configured to be separately received into the tapered bore of the femoral head component, wherein each of the plurality of femoral stem components has (i) a length that is different from at least some of the other plurality of femoral stem components, (ii) a trunnion taper angle and diameter that is the same as each of the other of the plurality of femoral stem components, (iii) an anterior/posterior stem taper angle that is different from at least some of the other of the plurality of femoral stem components, and (iv) a medial/lateral stem taper angle that is the same as each of the other of the plurality of femoral stem components, wherein a first femoral stem component of the plurality of femoral stem components (i) is longer than a second femoral stem component and a third femoral stem component of the plurality of femoral stem components, (ii) has a larger anterior/posterior stem taper angle than the second femoral stem component of the plurality of femoral stem components, and (iii) has an anterior/posterior stem taper angle that is the same as the third femoral stem component of the plurality of femoral stem components.

13. The implantable orthopaedic hip prosthesis assembly of claim 12, wherein each of the plurality of femoral stem components further has a medial/lateral cross sectional stem shape that is the same as each of the other of the plurality of femoral stem components.

* * * * *